(12) United States Patent
Pickford et al.

(10) Patent No.: US 9,649,410 B2
(45) Date of Patent: May 16, 2017

(54) METAL IMPLANTS

(71) Applicant: Accentus Medical Limited, Didcot (GB)

(72) Inventors: Martin Edward Lee Pickford, Southampton (GB); Andrew Derek Turner, Abingdon (GB)

(73) Assignee: Accentus Medical Limited, Didcot (GB)

( * ) Notice: Subject to any disclaimer, the term of this patent is extended or adjusted under 35 U.S.C. 154(b) by 77 days.

(21) Appl. No.: 14/581,564

(22) Filed: Dec. 23, 2014

(65) Prior Publication Data

US 2015/0110844 A1     Apr. 23, 2015

Related U.S. Application Data

(60) Continuation of application No. 12/539,028, filed on Aug. 11, 2009, now Pat. No. 8,945,363, which is a division of application No. 10/501,538, filed as application No. PCT/GB03/01264 on Mar. 25, 2003, now Pat. No. 7,695,522.

(30) Foreign Application Priority Data

Apr. 16, 2002  (GB) .................................. 0208642.9

(51) Int. Cl.
| | |
|---|---|
| *C25D 11/26* | (2006.01) |
| *A61L 27/54* | (2006.01) |
| *A61F 2/30* | (2006.01) |
| *A61L 27/04* | (2006.01) |
| *A61L 27/30* | (2006.01) |
| *A61L 27/32* | (2006.01) |
| *C25D 11/02* | (2006.01) |
| *A61F 2/32* | (2006.01) |

(52) U.S. Cl.
CPC .......... *A61L 27/54* (2013.01); *A61F 2/30767* (2013.01); *A61L 27/04* (2013.01); *A61L 27/306* (2013.01); *A61L 27/32* (2013.01); *C25D 11/02* (2013.01); *C25D 11/26* (2013.01); *A61F 2/3094* (2013.01); *A61F 2/32* (2013.01); *A61F 2002/30929* (2013.01); *A61F 2002/30967* (2013.01); *A61F 2310/00017* (2013.01); *A61F 2310/00023* (2013.01); *A61F 2310/00029* (2013.01); *A61F 2310/0052* (2013.01); *A61F 2310/00089* (2013.01); *A61F 2310/00592* (2013.01); *A61F 2310/00598* (2013.01); *A61F 2310/00796* (2013.01); *A61L 2300/104* (2013.01); *A61L 2300/404* (2013.01); *A61L 2420/02* (2013.01); *A61L 2430/02* (2013.01)

(58) Field of Classification Search
CPC ......... A61L 27/32; A61L 27/54; C25D 11/26; A61F 2/30767
USPC .................................................. 205/200, 229
See application file for complete search history.

(56) References Cited

U.S. PATENT DOCUMENTS

| | | | | |
|---|---|---|---|---|
| 4,476,590 | A * | 10/1984 | Scales ................. | A61B 17/866 606/76 |
| 6,191,192 | B1 * | 2/2001 | Monden ................ | A01N 25/34 523/122 |
| 6,582,715 | B1 | 6/2003 | Barry et al. | |
| 2002/0099449 | A1 * | 7/2002 | Speitling ............. | A61F 2/30767 623/23.72 |
| 2003/0091612 | A1 * | 5/2003 | Sabesan ................ | A01N 25/34 424/423 |

FOREIGN PATENT DOCUMENTS

SE    WO 9851231 A1 *  11/1998 ........... A61C 8/0012

* cited by examiner

*Primary Examiner* — Christopher D Prone
(74) *Attorney, Agent, or Firm* — Christensen O'Connor Johnson Kindness PLLC

(57) ABSTRACT

A metal implant for use in a surgical procedure is provided with a surface layer that is integral with the metal substrate, and which incorporates a biocidal material. The surface layer may be grown from the metal substrate, by anodising, and the biocidal material incorporated in it by ion exchange. Alternatively the layer may be deposited by electroplating, followed by diffusion bonding so as to become integral with the metal substrate. In either case, silver is a suitable biocidal material; and both the release rate and the quantity of biocidal material should be low to avoid toxic effects on body cells. Electropolishing the surface before formation of the surface layer is also beneficial, and this may be achieved by electropolishing.

7 Claims, No Drawings

METAL IMPLANTS

CROSS-REFERENCES TO RELATED APPLICATIONS

This application is a continuation of U.S. patent application Ser. No. 12/539,028, filed Aug. 11, 2009, now U.S. Pat. No. 8,945,363, which is a divisional of U.S. patent application Ser. No. 10/501,538, filed Jul. 16, 2004, now U.S. Pat. No. 7,695,522, which is a National Stage of PCT/GB03/01264, filed Mar. 25, 2003, the entire disclosures of which are incorporated herein by reference.

BACKGROUND

Field of the Invention

This invention relates to metal implants for use in surgical procedures, and in particular to the introduction of a biocidal material into such implants to suppress or control infection.

Background of the Invention

Various surgical procedures require the use of implants. For example cancerous bone may be removed, in prosthetic surgery, to be replaced by a metal implant. Such an implant may for example be of titanium alloy, which is very strong and relatively light. To ensure a hard-wearing surface the provision of a titanium nitride coating has been suggested. There is furthermore a risk of introducing infection when implanting such metal implants, and it has been suggested that metallic silver might be electroplated onto metal implants, the silver being a biocidal material that can control infection without causing toxic effects to the patient. However such coatings, whether of titanium nitride or silver, may be undercut due to corrosion from body fluids, so that the coating may detach from the implant, which may can increase wear and cause tissue damage.

BRIEF SUMMARY OF SOME OF THE PREFERRED EMBODIMENTS

According to the present invention there is provided an implant for use in a surgical procedure, the implant comprising a metal substrate and a surface layer that is integral with the metal substrate, the layer incorporating a biocidal metal deposited from a solution.

The invention also provides a method of producing such an implant.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other embodiments for carrying out the same purposes of the present invention. It should also be realized by those skilled in the art that such equivalent embodiments do not depart from the spirit and scope of the invention as set forth in the appended claims.

DETAILED DESCRIPTION OF THE PREFERRED EMBODIMENTS

Such an integral surface layer may be generated by growing the layer from the metal itself, for example by an anodising process; or alternatively by depositing the layer for example by electroplating, followed by diffusion bonding so that the layer becomes integral with the metal of the implant. Anodising forms an adherent oxide layer, although if it is carried out in phosphoric acid then a phosphate may be formed. Such an adherent phosphate layer may also be modified to form a hydroxyapatite layer, which can stimulate bone growth.

The biocidal material should preferably be effective for at least 6 weeks, preferably for up to 6 months after surgery, and the release rate should be low to avoid toxic effects on body cells. Furthermore the total quantity of biocidal material is preferably also limited to minimize any toxic effects.

It is also desirable if the surface is highly polished before production of the surface layer. This may for example be achieved by electropolishing.

In principle, a range of different metals may be used for the biocidal metal. In particular, if the layer is a metal layer deposited by electroplating then it clearly must be stable to corrosion. Gold, platinum, iridium and palladium would be potentially suitable, although expensive; silver is preferable as it is not particularly soluble in body fluids due to the presence of chloride ions and the low solubility of silver chloride. If the surface layer contains the biocidal metal in ionic form, then a wider range of metals would be possible. In addition to the elements already mentioned, copper, tin, antimony, lead, bismuth and zinc might be used as ions combined into an insoluble matrix for example of metal oxide or metal phosphate. The rate of release would be controlled, in this case, primarily by the strength of the absorption of the metal ions in the matrix.

The metals that may be used to make such prosthetic implants are typically a form of stainless steel, a titanium alloy, or a cobalt/chromium alloy, although zirconium could also be used. The standard alloys for this purpose are titanium 90% with 6% aluminium and 4% vanadium (British standard 7252), or chromium 26.5-30%, molybdenum 4.5-7%, and the remainder cobalt (British standard 7252 part 4).

Preferably the implant is initially polished to provide a very smooth surface. Both stainless steel (chromium/iron/nickel) and cobalt/chromium alloy can be electro-polished using as electrolyte a mixture of phosphoric acid and glycerine, or a mixture of phosphoric acid and sulphuric acid. Titanium alloy can be electro-polished using acetic acid, or a mixture of nitric and hydrofluoric acids. Alternatively the implants might be subjected to a combination of anodic passivation with mechanical polishing, which may be referred to as electrolinishing, this process removing the oxide that protects surface roughness, the surface at that point then being electrochemically re-passivated, so producing a mirror-smooth finish. Various electrolytes are suitable for this purpose, including nitric acid mixed with sulphuric acid, sodium hydroxide, sodium phosphate, or sodium hydroxide mixed with sodium nitrate.

After polishing the surface of the metal, either silver deposition or surface conversion can take place. Considering surface conversion first, a layer of metal oxide or phosphate may be formed by anodising in a suitable electrolyte, so that the oxide or phosphate layer builds out from the surface of the metal. Biocidal metal ions can then be absorbed from an aqueous salt solution into the oxide or phosphate matrix, for example the ions $Ag^+$ or $Cu^{++}$. Cations of palladium, platinum or even ruthenium could be absorbed in a similar way. If desired, deposited silver, platinum or palladium ions could then be converted to metal, or deposited ruthenium ions converted to insoluble $RuO_2$, within the oxide or phosphate surface coating, this reaction being performed chemically or electrochemically or by light.

Considering now silver deposition, the coating should be thin to prevent toxic effects. A high degree of adherence to the underlying metal can be ensured by first removing the surface oxide layer by anodic etching, followed by a brief reversal of polarity in the presence of appropriate ions, so as to cover the surface with a thin coating of silver. This may be repeated to ensure there are no pin-holes. The plating electrolyte may include hydrofluoric acid, or may be an alkaline cyanide electroplating electrolyte. After deposition, the silver coating should be diffusion bonded so as to form an inter-metallic layer, by heating the implant to an elevated temperature. Typically it should be heated to above 800° C., preferably between 810° C. and 950° C., in an inert atmosphere for example of argon for a period of between 1 and 6 hours. This substantially eliminates the risk of coating delamination. However with titanium-based implants the temperature must not exceed 850° C. as titanium would undergo a phase change from alpha to beta form above this temperature.

In place of silver, other metals such as platinum or palladium may be electro-deposited and then thermally treated in a similar fashion so as to form an inter-metallic layer.

The invention will now be further and more particularly described, by way of example only.

A hip implant is made of titanium alloy (Ti/Al/V). The implant is cleaned ultrasonically using first acetone as the liquid phase, and then a 1 M aqueous solution of sodium hydroxide, and is then rinsed in de-ionised water. The cleaned implant is then immersed in a stirred 12 weight % solution of phosphoric acid, and is anodised for 2 hours at a maximum voltage of 10 V and a maximum current of 10 mA/cm$^2$, so as to form a surface coating of titanium phosphate. It is then rinsed in de-ionised water again. The surface, which is initially pale grey, turns to a darker matt grey as a consequence of the anodising, with a slightly yellow hue.

The implant is then immersed in a stirred 0.1 M aqueous solution of silver nitrate, and left for 2 hours. As a result of ion exchange there is consequently some silver phosphate in the titanium phosphate coating. The implant is then ready to be implanted. During exposure to body fluids there will be a slow leaching of silver ions from the phosphate layer, so that any bacteria in the immediate vicinity of the implant are killed. Infection arising from the implant is therefore suppressed.

Experimental samples of this titanium alloy were cleaned, anodised to form a layer of titanium phosphate, and then subjected to ion exchange to form silver phosphate, following the procedure described above. One sample was placed in direct daylight for 110 hours; the exposed surface became darkened as a result of this exposure to daylight, indicating the formation of silver metal by photo-reduction. The other sample was immersed in a solvent containing a mixture of 4 M nitric acid and 0.5 M sodium fluoride (equivalent to hydrofluoric acid) to dissolve the coating. The dark grey surface coating was removed completely within 3 minutes, leaving a silver-grey finish. The resulting solution was analyzed for the presence of silver by atomic absorption spectrometry, and the concentration of silver was found to be equivalent to an average surface loading of 73 µg/cm$^2$.

The present invention further provides the following additional embodiments:

[1] An implant for use in a surgical procedure, the implant comprising a metal substrate and a surface layer that is integral with the metal substrate, the layer incorporating a biocidal metal deposited from a solution.

[2] An implant as defined in [1] wherein the integral surface layer is generated by growing the layer from the metal.

[3] An implant as defined in [2] wherein the surface layer is generated by an anodising process.

[4] An implant as defined in [3] wherein the surface layer comprises a metal phosphate.

[5] An implant as defined in any one of [2] to [4] wherein the biocidal metal comprises metal ions absorbed within the surface layer.

[6] An implant as defined in [5] wherein the biocidal material comprises silver.

[7] An implant as defined in [1] wherein the integral surface layer is generated by first depositing the layer and then subjecting the layer and the substrate to diffusion bonding so that the layer becomes integral with the metal of the substrate.

[8] An implant as defined in any one of [1] to [7] wherein the surface of the implant is highly polished before provision of the surface layer.

[9] A method of making an implant for use in a surgical procedure, the implant comprising a metal substrate, and the method comprising forming a surface layer on the substrate which is integral with the metal substrate, and incorporating a biocidal metal in the layer by deposition from a solution.

[10] A method as defined in [9] comprising anodising the surface of the substrate to form the integral surface layer.

[11] A method as defined in [10] wherein silver ions are incorporated in the surface layer by contact with a solution containing silver ions.

[12] A method as defined in [9] wherein the surface layer is a metal layer deposited by electroplating, and is subsequently rendered integral with the substrate by a heat treatment to cause diffusion bonding.

Although the present invention and its advantages have been described in detail, it should be understood that various changes, substitutions and alterations may be made herein without departing from the spirit and scope of the invention as defined by the appended claims.

The embodiments of the invention in which an exclusive property or privilege is claimed are defined as follows:

1. An implant for use in a surgical procedure, the implant comprising a metal substrate, wherein the implant comprises an anodised surface layer that is integral with the metal substrate, the anodised surface layer comprising a phosphate and biocidal metal ions, such that, after implantation, leaching of the biocidal metal ions kills bacteria in the vicinity of the implant and suppresses infection.

2. The implant of claim 1, wherein the biocidal metal ions are selected from the group consisting of silver, palladium, platinum and ruthenium.

3. The implant of claim 1, wherein the biocidal metal ions are of silver.

4. The implant of claim 1, wherein the biocidal metal ions comprised in the anodised surface layer are absorbed into the anodised surface layer by ion exchange.

5. The implant of claim 1, wherein the anodised surface layer that is integral with the metal substrate is grown by an anodising process that is carried out using a solution of phosphoric acid.

6. The implant of claim 5, wherein the biocidal metal ions comprised in the anodised surface layer are absorbed by ion exchange into the anodised surface layer that is integral with the metal substrate that is grown by the anodising process that is carried out using the solution of phosphoric acid.

7. The implant of claim 1, wherein the implant is obtained by a method comprising the successive steps of:

(A) forming an anodised surface layer on the metal substrate which is integral with the metal substrate by growing the layer by an anodising process that is carried out using a solution of phosphoric acid, wherein the anodised surface layer comprises a phosphate;
(B) rinsing the anodised surface layer obtained on the substrate that is obtained in (A); and
(C) contacting the anodised surface layer on the substrate that is obtained in (B) with a solution that contains biocidal metal ions, so as to absorb biocidal metal ions by ion exchange into the anodised surface layer, thereby forming a phosphate comprising at least one biocidal metal ion, wherein after contacting with the solution that contains biocidal metal ions, the implant is ready to be implanted.

* * * * *